US004001630B2

United States Statutory Invention Registration [19]

[11] Reg. Number: H1630

[45] Published: Jan. 7, 1997

Roe et al.

[54] DIAPER HAVING PLURAL UPSTANDING LEG CUFFS

[75] Inventors: Donald C. Roe, West Chester; Kimberly A. Dreier, Cincinnati, both of Ohio

[73] Assignee: The Procter & Gamble Company, Cincinnati, Ohio

[21] Appl. No.: 396,949

[22] Filed: Mar. 1, 1995

[51] Int. Cl.[6] ..... A61F 13/15

[52] U.S. Cl. ..... 604/385.2

[58] Field of Search ..... 604/385.2

[56] References Cited

U.S. PATENT DOCUMENTS

| | | | |
|---|---|---|---|
| 3,860,003 | 1/1975 | Buell | 128/287 |
| 4,425,129 | 1/1984 | Karami | 604/385 |
| 4,636,207 | 1/1987 | Buell | 604/370 |
| 4,695,278 | 9/1987 | Lawson | 604/385 A |
| 4,808,177 | 2/1989 | Desmarais et al. | 604/385.1 |
| 4,904,251 | 2/1990 | Igaue et al. | 64/385.2 |
| 4,909,803 | 3/1990 | Aziz et al. | 7604/385.2 |
| 5,032,120 | 7/1991 | Freeland et al. | 604/385.2 |
| 5,167,653 | 12/1992 | Igaue et al. | 604/385.2 |
| 5,190,606 | 3/1993 | Merkatoris et al. | 156/164 |
| 5,246,431 | 9/1993 | Minetola et al. | 604/385.2 |
| 5,304,159 | 4/1994 | Tanji et al. | 604/385.2 |
| 5,403,301 | 4/1995 | Huffman et al. | 604/385.2 |

FOREIGN PATENT DOCUMENTS

| | | | |
|---|---|---|---|
| 71521 | 5/1990 | Japan | 604/385.2 |
| 152450 | 6/1990 | Japan | 604/385.2 |
| 174845 | 7/1990 | Japan | 604/385.2 |
| 218752 | 9/1991 | Japan | 604/385.2 |
| 99921 | 8/1992 | Japan | 604/385.2 |
| 3889 | 1/1993 | Japan | 604/385.2 |

*Primary Examiner*—Michael J. Carone
*Assistant Examiner*—Theresa M. Wesson
*Attorney, Agent, or Firm*—Larry L. Huston; E. Kelly Linman; Jacobus C. Rasser

[57] ABSTRACT

A disposable absorbent article such as a diaper. The diaper has dual upstanding inner and outer barrier leg cuffs, and preferably gasket cuffs. The inner barrier leg cuffs are liquid pervious, while the outer barrier leg cuffs are liquid impermeable. The inner barrier leg cuffs are preferably spaced apart from one another sufficient to allow urine and fecal material to be deposited therebetween. Each outer barrier leg cuff is preferably spaced properly from the inner barrier leg cuff so as to allow the leg cuffs to function independently, yet maintain a proper target area for the deposition of urine and fecal material.

13 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

DIAPER HAVING PLURAL UPSTANDING LEG CUFFS

FIELD OF THE INVENTION

This invention is related to disposable absorbent articles, particularly to disposable absorbent articles such as diapers, which receive fecal material, and more particularly to diapers having upstanding leg cuffs.

BACKGROUND OF THE INVENTION

Disposable absorbent articles, such as diapers, are well known in the art. These articles address the consumers' demands for increased convenience. In particular, disposable absorbent articles which minimize cleaning of the wearer after the article is soiled provide convenience. A particularly desired feature in such diapers is the prevention or minimization of leakage of urine and fecal material received by the diaper.

Several attempts in the art have been very successful at reducing leakage from the diaper. One early attempt provided an elastic contracting member, which elastically contracted the outer side portion of the diaper. This highly successful advance in the art provided a gasket leg cuff. The gasket leg cuff was disposed in the plane of the diaper. The next attempt provided a diaper having elasticized flaps, known as barrier leg cuffs. Barrier leg cuffs stand up out of the plane of the diaper and thereby improve containment. Yet other attempts in the art included diapers with dual cuffs, including both a gasket leg cuff and a barrier leg cuff. Yet other advances in the art provided leg cuffs with relatively low contact forces against the skin of the wearer at relatively high elongations, minimizing wearer discomfort.

Examples of such attempts in the art can be found in commonly assigned U.S. Pat. Nos. 3,860,003 issued Jan. 14, 1975 to Buell; 4,695,278 issued Sep. 22, 1987 to Lawson; 4,909,803 issued Mar. 20, 1990 to Aziz et al.; and 5,032,120 issued Jul. 16, 1991 to Freeland et al., which patents are incorporated herein by reference.

However, there is a need in the art for diapers which further reduce leakage. There is further a need in the art for such a diaper which minimizes leakage of fecal material from the leg region.

SUMMARY OF THE INVENTION

The invention comprises a diaper having a longitudinal centerline and a lateral centerline orthogonal to the longitudinal centerline. The diaper has a liquid pervious topsheet, a liquid impermeable backsheet at least partially peripherally joined to the topsheet, and an absorbent core intermediate the topsheet and the backsheet.

Upstanding from the plane of the topsheet are two generally longitudinally oriented liquid impervious outer barrier leg cuffs. One of the outer barrier leg cuffs is disposed on each side of the longitudinal centerline. Also upstanding from the plane of the topsheet are two generally longitudinally oriented liquid pervious inner barrier leg cuffs. One of each of the inner barrier leg cuffs is also disposed on each side of the longitudinal centerline. Each of the inner barrier leg cuffs is disposed between the corresponding outer barrier leg cuff and the longitudinal centerline. Each of the outer barrier leg cuffs is outboard of and preferably spaced apart from the corresponding inner barrier leg cuff 0.5 to 2.0 inches.

DETAILED DESCRIPTION OF THE INVENTION

As used herein, the term "absorbent article" refers to devices which absorb and contain body exudates and are placed against or in proximity to the body of the wearer to absorb and contain discharges. The term "disposable" describes absorbent articles not intended to be laundered or otherwise restored or reused (i.e., they are intended to be discarded after a single use and preferably recycled, composted, or otherwise disposed of in an environmentally compatible manner). A "unitary" absorbent article refers to an article formed of separate pans united together to form a coordinated entity that does not require separate manipulative parts, like a separate holder and liner. A preferred embodiment of a disposable absorbent article of the present invention is the unitary disposable absorbent article, diaper 20, shown in FIG. 1. As used herein the term "diaper" refers to a disposable absorbent article generally worn by infants and incontinent persons about the lower torso. It should be understood, however, that the present invention is also applicable to other disposable absorbent articles such as incontinence briefs, incontinence undergarments, and diaper holders and liners.

Figure 1:
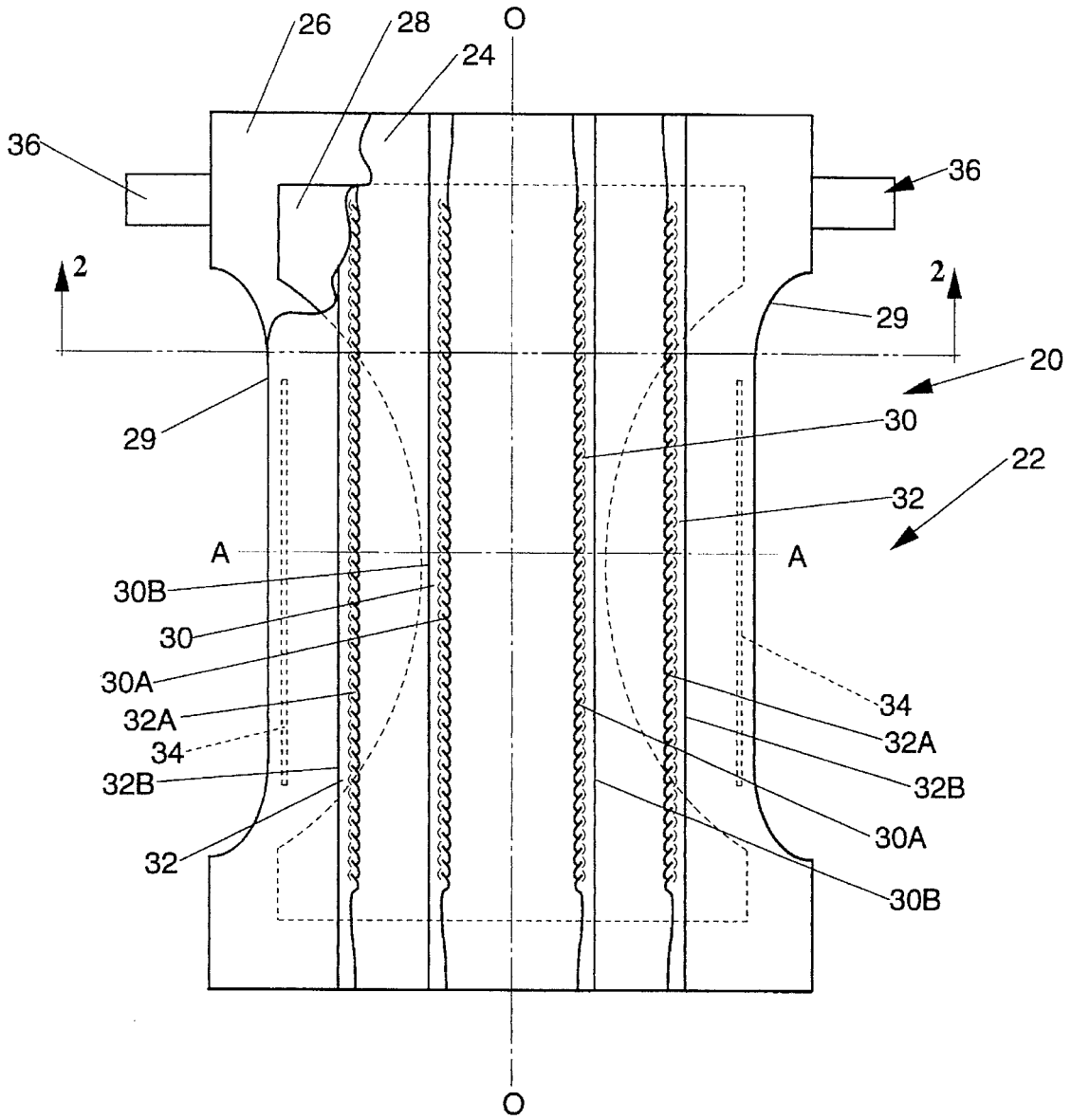
FIG. 1 is a top plan view, shown partially in cutaway, of a diaper according to the present invention.

FIG. 1 is a plan view of diaper 20 of the present invention in its flat, uncontracted state (with elastic induced contraction pulled out, and portions of the structure cut away to more clearly show the construction of the diaper 20). The portion of the diaper 20 which faces or contacts the wearer, i.e., the inner surface, is oriented towards the viewer. The diaper 20 has a longitudinal centerline O—O and a lateral centerline A—A. As used here in the longitudinal centerline O—O or dimension is aligned front to back and bisects the standing wearer into left and right body halves. The lateral centerline A—A or dimension is orthogonal the longitudinal centerline O—O and lies within the plane of the diaper 20. The Z-direction is orthogonal to both the longitudinal and lateral directions and comes out of the plane of the diaper 20.

The diaper 20 has a chassis 22 comprising a liquid pervious topsheet 24, a liquid impermeable backsheet 26 at least partially peripherally joined to the topsheet 24, and an absorbent core 28 between the topsheet 24 and the backsheet 26. The topsheet 24 has an inwardly oriented surface which is oriented towards the core 28, and an outwardly oriented surface which is oriented towards and/or contacts the wearer. Upstanding from the plane of the top sheet 24 are a set of inner barrier leg cuffs 30, and a set of outer barrier leg cuffs 32. Outboard of the outer barrier leg cuffs 32 and in line within the plane of the diaper 20 are gasket cuffs 34. As used herein, "outboard" refers to either lateral direction which is oriented away from the longitudinal centerline O—O.

The diaper 20 may also include tape fasteners 36 positioned in the rear waist region for fastening the diaper 20 about the wearer. The diaper 20 can also have an elastic waistband (not shown). Commonly assigned U.S. Pat. Nos. 3,848,594 issued Nov. 19, 1974 to Buell; Re. B1 4,662,875 issued May 5, 1987 to Hirotsu et al. are incorporated herein by reference to illustrate tape fasteners 36; and 4,515,959 issued May 17, 1985 to Kiev; and 4,816,025 issued Mar. 28, 1989 to Foreman, are incorporated herein by reference to illustrate elasticized waist features.

The top sheet 24 and backsheet 26 of the diaper 20 have longitudinal and lateral dimensions generally larger than those of the absorbent core 28, so that the topsheet 24 and backsheet 26 may extend beyond the core 28 to thereby form the periphery 29 of the diaper 20. The embodiment described herein is suitable for a wearer weighing about 7.3 to about 12.7 kilograms (16 to 28 pounds). It will be understood that if the diaper 20 is intended for use with larger or smaller wearers, including adults, or if the diaper 20 is closed in a training pants style, the diaper 0, including the inner and outer barrier leg cuffs 30, 32, may have to be scaled accordingly.

Examining the components of the diaper 20 in more detail, the topsheet 24 and backsheet 26 are generally coextensive and at least partially peripherally joined. As used herein, the term "joined" refers to the condition where a first member or component is affixed or connected to a second member or component, either directly or indirectly where the first member or component is directly affixed to the second member or component, or connected to an intermediate member or component which in turn is affixed or connected to the second member or component. Components which are "joined" are intended to remain affixed or connected throughout the intended life of the diaper 20 and not to be separated unless and until the diaper 20 is discarded and as may be necessary for environmentally compatible disposal. Components which are "joined" cannot be separated without tearing or gross deformation of one or both components.

The topsheet 24 refers to any liquid pervious facing of the diaper 20 which contacts the skin of the wearer and prevents substantial contact of the absorbent core 28 with the skin of the wearer. The topsheet 24 is compliant, tactilely pleasant, and non-irritating to the skin.

A suitable topsheet 24 may be manufactured from porous foams, apertured plastic films, natural fibers, synthetic fibers, or a combination thereof. A particularly preferred topsheet 24 comprises polypropylene fibers and may be manufactured as a nonwoven web of spunbonded, carded, wet laid, melt blown, hydroentangled fibers. A particularly preferred topsheet 24 is carded and thermally bonded to have a basis weight of 14 to 25 grams per square meter. A suitable topsheet 24 is marketed by Veratec Inc., Division of International Paper Company, of Walpole, Mass. under the designation P-8.

The backsheet 26 is impermeable to fluids such as urine and prevents fluids absorbed and contained by the core 28 from wetting the undergarments. As used herein, the "backsheet" refers to any barrier disposed outwardly of the core 28 as the diaper 20 is worn and which contains absorbed liquid within the diaper 20. The backsheet 26 is preferably manufactured from a thin plastic film, although other flexible, liquid impermeable materials may be used. As used herein, the term "flexible" refers to materials which are compliant and will readily conform to the general shape of the human body.

The backsheet 26 may be a polyolefinic film, such as polyethylene, having a thickness of about 0.01 to 0.05 millimeters. A suitable backsheet 26 can be made from a blend of 45 to 90 percent LLDP and about 10 to 55 percent polypropylene. Exemplary backsheet films are sold by Tredegar Industries of Terre Haute, Ind. under the designation RR8220 and RR5475.

The topsheet 24 and backsheet 26 may be joined by any means well known in the art, such as adhesive bonding or heat sealing. A particularly preferred method of joining the topsheet 24 and backsheet 26 is with hot melt adhesives such as are manufactured by Century Adhesives, Inc. of Columbus, Ohio and marketed as Century 5227, or BL1258 adhesive sold by the H. B. Fuller Company of St. Paul, Minn., or H2031 available from the Findley Adhesives Company of Elmgrove, Wisc.

As used herein, the term "core" refers to any component of the diaper 20 intermediate the topsheet 24 and backsheet 26 and used for absorbing and retaining body exudates. The core 28 may be encased by one or more layers of tissue (not shown).

The absorbent core 28 may be made from a variety of materials such as comminuted wood pulp and may further contain particulate or fibrous absorbent gelling materials as are commonly known in the art. The absorbent core 28 may be made in accordance with the teachings of commonly assigned U.S. Pat. Nos. 4,610,678 issued Sep. 9, 1986 to Weisman et al.; 5,137,537 issued Aug. 11, 1992 to Herron et al.; and 5,147,345 issued Sep. 15, 1992 to Young et al., which patents are incorporated herein by reference. Absorbent gelling materials, if desired, may be made in accordance with commonly assigned U.S. Pat. Re. 32,649, reissued Apr. 19, 1988 to Brandi et al.

Figure 2:
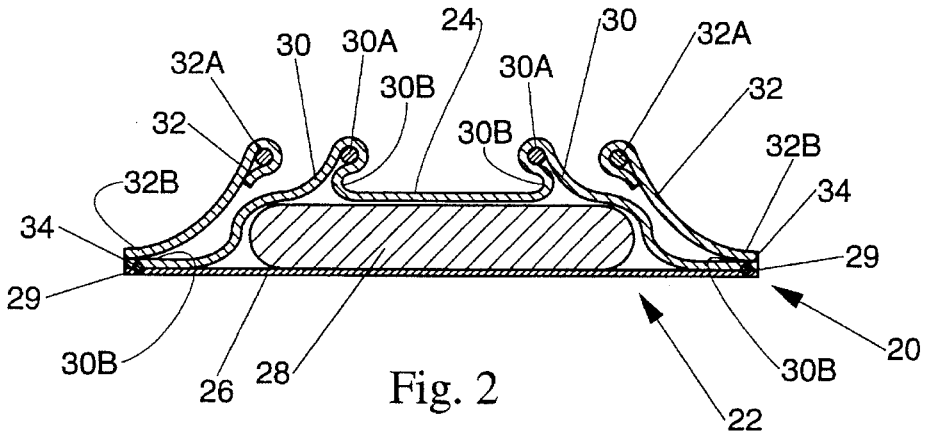
FIG. 2 is an instantaneous vertical sectional view taken along lines 2—2 of FIG. 1.

Referring to FIG. 2, the inner barrier leg cuffs 30 may, in part, overlie the core 28 and are generally longitudinally oriented. Preferably each inner barrier leg cuff 30 is laterally spaced a distance of 2.0 to 3.5 inches from the other inner barrier leg cuff 30. Such spacing is taken at the proximal edges 30B of the inner barrier leg cuffs 30. Generally, for the embodiment described herein, this spacing is critical for proper performance of the diaper 20. Such a spacing is necessary to allow sufficient room for urine and fecal material to be deposited on the topsheet 24 at a position intermediate the inner barrier leg cuffs 30. Therefore, the inner barrier leg cuffs 30 should not be spaced any closer together than this range. Likewise, the inner barrier leg cuffs 30 should not be spaced too far apart, otherwise the inner barrier leg cuffs 30 will be too close to the outer barrier leg cuffs 32, as discussed below.

The inner barrier leg cuffs 30 are preferably elastically contractible due to elastic strands 30A joined to the inner barrier leg cuffs 30. The elastic strands 30A may be made using any type of elastic as is well known in the art. Of course, elastic strands 30A, 32A include elastomeric films, elastomeric adhesives, as well as elastic strands, and combinations thereof. The inner barrier leg cuffs 30 may have an elasticized length in the longitudinal direction of about 8 to 15 inches. The elastic strands 30 may have a force of 10 to 30 grams, and preferably 15 to 25 grams, at 85 percent elongation. Preferably the inner barrier leg cuff 30 extends 0.5 to 1.25 inches above the plane of the topsheet 24 to a distal edge.

The inner barrier leg cuffs 30 are preferably hydrophilic and liquid pervious. These material properties are critical in that they allow urine deposited on the topsheet 24 to laterally migrate through the inner barrier leg cuffs 30 so that full utilization of the capacity of the absorbent core 28 is possible. Conversely, if the inner barrier leg cuffs 30 were liquid impervious, urine would pool between the inner barrier leg cuffs 30, irritating the skin of the wearer and may lead to premature leakage. An additional benefit of a hydrophilic pervious inner barrier leg cuff 30 is that low viscosity fecal material which contacts the inner barrier leg cuff 30 may be partitioned into solid components which are contained between the inner barrier leg cuffs 30 and liquid components which permeate the inner barrier leg cuffs 30. By partitioning the low viscosity fecal material in this manner, the likelihood of it leaking is reduced.

Preferably the inner barrier leg cuffs 30 are made of a nonwoven material, as is available from the Veratec Company of Walpole, Mass. The inner barrier leg cuffs 30 may be adhesively joined to the topsheet 24 as is well known in the art. The distal end of the inner barrier leg cuff may be joined to the topsheet 24 at the waist margins of the diaper 20, as shown. The upstanding portion of the inner barrier leg cuff 30 may be liquid impervious, in part, so long as urine can pass through at least a portion thereof, and the proximal edge 30B does not prevent urine from passing into the topsheet 24.

Each outer barrier leg cuff 32 is preferably spaced 0.5 to 2.0 inches laterally outboard (i.e., away from the longitudinal centerline O—O) of its corresponding inner barrier leg cuff 30. Such spacing is taken at the proximal edge 32B of the outer barrier leg cuff 32. Inner barrier leg cuffs 30, outer barrier leg cuffs 32, and gasket cuffs 34 are said to be "corresponding" if they are disposed on the same side of the longitudinal centerline O—O.

It is, of course, recognized that the inner and outer barrier leg cuffs 30, 32 may not always be straight and parallel, as shown. Instead, one set of barrier leg cuffs 30, 32 may be longitudinally oriented as shown, and the other set of barrier leg cuffs 32, 30 be in angular relationship therewith. For purposes of the present invention, the spacing criterion is met if at least 33 percent of the upstanding portions of the inner and outer barrier leg cuffs 30, 32 fall within the aforementioned range of 0.5 to 2.0 inches. Although a minimum of 50 percent effective spacing is preferred, at least 75 percent is more preferred. Preferably, the aforementioned spacing is met at the rear portion of the diaper 20 because this is most typically where fecal material is loaded.

This spacing between the inner and outer barrier leg cuffs 30, 32 is critical. If the inner and outer barrier leg cuffs 30, 32 are spaced too close together, they will function as a single barrier leg cuff and not be effective at reducing leakage. Likewise, the distal ends of the inner and outer barrier leg cuffs 30, 32 must be separated, and not joined together, otherwise they will function like a single leg cuff. Conversely, the outer barrier leg cuff 32 cannot be spaced further from the inner barrier leg cuff 30 than the constraints imposed by the periphery 29 of the diaper 20. As noted above, once the periphery 29 of the diaper 20 is fixed, the inner barrier leg cuffs 30 (as measured between the proximal edges 30) cannot be moved closer together, otherwise the urine and fecal material may be deposited on the inner barrier leg cuffs 30, or between the inner and outer barrier leg cuffs 30, 32. If either occurs, leakage is more likely to result.

The outer barrier leg cuffs 32 are preferably elastically contractible due to elastic strands 32A joined to the outer barrier leg cuffs 32. The elastic strands 32A may be made using any type of elastic as is well known in the art. The outer barrier leg cuffs 32 may have an elasticized length taken in the longitudinal direction of about 8 to 15 inches, and have a force of 30 to 65 grams, and preferably 40 to 50 grams at 85 percent elongation.

It is important that the outer barrier leg cuffs 32 have a greater contractive force under a given elongation than the inner barrier leg cuffs 30, so that a tighter seal is formed at the leg of the wearer. Additionally, the inner leg cuffs 30 typically intercept the skin of the wearer at a position of the body more prone to red marking, and the discomfort attendant therewith. Therefore, less force should be applied by the inner barrier leg cuff 30 than the outer barrier leg cuff 32.

Preferably the outer barrier leg cuffs 32 extend 0.75 to 2.0 inches above the plane of the topsheet 24. The outer barrier leg cuffs 32 preferably extend further in the Z-direction than the inner barrier leg cuffs 30, so that overflow past the inner barrier leg cuffs 30 does not reach a second barrier leg cuff 32 of the same height and allow leakage. Also, this greater Z-direction extent is necessary to accommodate the curvature of the buttocks of the wearer.

It is critical that the outer barrier leg cuff 32 be hydrophobic and/or liquid impervious in order that any urine, low viscosity fecal material, or components of low viscosity fecal material which permeated the inner barrier leg cuff 30 is retained inboard (i.e., towards the longitudinal centerline O—O) of the outer barrier leg cuffs 32 so that leakage does not result. The outer barrier leg cuffs 32 may be made of a nonwoven material such as is available from Fiberweb Company of Simpsonville, S.C.

Optionally, a gasket cuff 34 is included in the diaper 20. The gasket cuff 34 may be spaced inboard or outboard of the outer barrier leg cuff 32 so long as the gasket cuff 34 is outboard of the inner barrier leg cuff 30. Preferably the gasket cuff 34 is outboard of the outer barrier leg cuff 32, so that the periphery 29 of the diaper 20 more readily conforms to the shape of the buttocks, and so that it is spaced far enough from the absorbent core 28 to be effective. In an alternative embodiment (not shown), the gasket cuff 34 may be positioned between the inner barrier leg cuff 30 and the outer barrier leg cuff 32. While the present invention does allow for bringing the gasket cuff 34 to within less than 0.75 inches of the edge of the absorbent core 28, contrary to important teachings in the prior art, such a spacing is generally not preferred.

What is claimed is:

1. A diaper having a longitudinal centerline, a lateral centerline orthogonal thereto, and a Z-direction perpendicular to said longitudinal centerline and said lateral centerline said diaper comprising:

a liquid pervious topsheet;

a liquid imperious backsheet at least partially peripherally joined to said topsheet;

an absorbent core intermediate said topsheet and said backsheet;

two generally longitudinally oriented outer barrier leg cuffs, upstanding from the plane of said topsheet, one of said outer barrier leg cuffs being disposed on each side of said longitudinal centerline;

two generally longitudinally oriented inner barrier leg cuffs upstanding from the plane of said topsheet, one of said inner barrier leg cuffs being disposed on each side of said longitudinal centerline, so that each said inner barrier leg cuff is disposed on the same side of said longitudinal centerline as one of said outer barrier leg cuffs corresponding thereto, each said corresponding outer barrier leg cuff and said corresponding inner barrier leg cliff being spaced apart 0.5 inches to 2.0 inches, said outer barrier leg cuffs having a greater extent in the Z-direction than said inner barrier leg cuffs; and two gasket cuffs lying within the plane of said diaper, one said gasket cuff being disposed on each side of said longitudinal centerline.

2. A diaper according to claim 1 wherein said inner barrier leg cuffs are spaced apart 2.0 to 3.5 inches.

3. A diaper according to claim 1 wherein each said gasket cuff is disposed outboard of said inner barrier leg cuff disposed on the same side of said longitudinal centerline as said gasket cuff.

4. A diaper according to claim 3 wherein each said gasket leg cuff is disposed outboard of said outer barrier leg cuff disposed on the same side of said longitudinal centerline as said gasket cuff.

5. A diaper according to claim 4 wherein said inner barrier leg cuffs have an elastic force at 85 percent elongation of 15 to 25 grams.

6. A diaper according to claim 4 wherein said outer barrier leg cuffs have an elastic force at 85 percent elongation of 40 to 50 grams.

7. A diaper having a longitudinal centerline, a lateral centerline orthogonal thereto, and a Z-direction perpendicular to said longitudinal centerline and said lateral centerline said diaper comprising;

a liquid pervious topsheet;

a liquid impervious backsheet at least partially peripherally joined to said topsheet;

an absorbent core intermediate said topsheet and said backsheet;

two generally longitudinally oriented liquid impervious outer barrier leg cuffs, upstanding from the plane of said topsheet, one of said outer barrier leg cuffs being disposed on each side of said longitudinal centerline;

two generally longitudinally oriented liquid pervious inner barrier leg cuffs upstanding from the plane of said topsheet, one of said inner barrier leg cuffs being disposed on each side of said longitudinal centerline, so that each said inner barrier leg cuff is disposed on the same side of said longitudinal centerline as one of said outer barrier leg cuffs corresponding thereto, said .outer barrier leg cuffs having a greater extent in the Z-direction than said inner barrier leg cuffs; and two gasket cuffs lying within the plane of said diaper, one said gasket cuff being ..disposed on each side of said longitudinal centerline.

8. A diaper according to claim 7 wherein said inner barrier leg cuffs are spaced apart 2.0 to 3.5 inches.

9. A diaper according to claim 8 whrein said outer barrier leg cuffs are hydrophobic.

10. A diaper according to claim 9 wherein said inner barrier leg cuffs have an elastic force at 85 percent elongation of 15 to 25 grams.

11. A diaper according to claim 10 wherein said outer barrier leg cuffs have an elastic force at 85 percent elongation of 40 to 50 grams.

12. A diaper according to claim 8 wherein said inner barrier leg cuffs are hydophilic.

13. A diaper according to claim 7 wherein each said gasket leg cuff is disposed outboard of said inner barrier leg cuff disposed on the same side of said longitudinal centerline as said gasket cuff.

* * * * *